US006432712B1

(12) United States Patent
Wolfinbarger, Jr.

(10) Patent No.: US 6,432,712 B1
(45) Date of Patent: Aug. 13, 2002

(54) TRANSPLANTABLE RECELLULARIZED AND REENDOTHELIALIZED VASCULAR TISSUE GRAFT

(75) Inventor: Lloyd Wolfinbarger, Jr., Norfolk, VA (US)

(73) Assignee: Bioscience Consultants, LLC, Norfolk, VA (US)

( * ) Notice: Subject to any disclaimer, the term of this patent is extended or adjusted under 35 U.S.C. 154(b) by 0 days.

(21) Appl. No.: 09/595,717

(22) Filed: Jun. 16, 2000

Related U.S. Application Data

(60) Provisional application No. 60/166,884, filed on Nov. 22, 1999.

(51) Int. Cl.[7] .................................................. C12N 5/00

(52) U.S. Cl. ........................ 435/395; 435/403; 435/373; 435/374

(58) Field of Search ................................. 435/395–483, 435/373, 374, 1.1, 1.2

(56) References Cited

U.S. PATENT DOCUMENTS 5,192,312 A * 3/1993 Orton
5,336,616 A * 8/1994 Livesey et al.
5,558,875 A * 9/1996 Wang
5,855,620 A * 1/1999 Bishopric et al.
5,899,937 A * 5/1999 Goldstein et al.

FOREIGN PATENT DOCUMENTS

WO WO-96/08213 A1 * 3/1996
WO WO-97/27885 A1 * 8/1997

OTHER PUBLICATIONS

Steinhoff et al., Tissue engineering of heart vavles on acellular matrix conduits (Nov. 2, 1999) Circulation, vol. 110, No. 18 SUPPL., p. I.528.*

Eybl et al. Endothelial clel lining of bioprosthetic heart valve materials (1992) J. Thorac. Cardiovasc. Surg., vol. 104, pp. 763–769.*

Bader et al., Tissue engineering of heart valves—human endothelial cell seeding of detergent acellularized porcine valves (1998) European Journal of Cardio–thoracic Surgery, vol. 14, pp. 279–284.*

Lehr et al., Rational for the use of antioxidant vitamins in clinical organ transplantation (Nov. 15, 1996) Transplantation, vol. 62, No. 9, pp. 1197–1199.*

Black et al., Tissue modifications (1998) Transplantation Proceedings, vol. 30, pp. 2729–2731.*

Wilson et al., Acellular matrix: a biomaterials approach for coronary artery bypass and heart valve replacement (1995) Ann. Thor. Surg., vol. 60, pp. S353–S358.*

Wilson et al., Acellular matrix allograft small caliber vascular protheses (1990) ASAIO Transactions, vol. 36, pp. M340–343.*

Courtman et al., Development of a pericardial acellular matrix biomaterial: biochemical and mechanical effects of cell extraction, (1994) Journal of Biomedical Materials Research, vol. 28, pp. 655–666.*

* cited by examiner

*Primary Examiner*—Jon P. Weber
(74) *Attorney, Agent, or Firm*—Crowell & Moring LLP

(57) ABSTRACT

The invention provides a device and process for recellularizing essentially acellular or devitalized tissue grafts, including for example essentially acellular or devitalized vascular tissue grafts, derived from human or animal sources, or as constructed using any number of tissue engineering methodologies. The process includes repopulating and reendothelializing an essentially acellular or devitalized tissue graft. The device is useful for producing a repopulated tissue graft from an essentially acellular or devitalized tissue, as well as for producing an essentially acellular or devitalized tissue graft.

74 Claims, 9 Drawing Sheets

TRANSPLANTABLE RECELLULARIZED AND REENDOTHELIALIZED VASCULAR TISSUE GRAFT

This application claims the benefit of U.S. provisional application No. 60/166,884, filed Nov. 22, 1999.

FIELD OF THE INVENTION

The invention provides a device and process for decellularizing, and/or devitalizing, tissue grafts; and/or recellularizing, essentially acellular or devitalized tissue grafts, including for example essentially acellular or devitalized vascular tissue grafts, where the graft is derived from a human or animal sources, or is as constructed using any number of tissue engineering methodologies.

BACKGROUND OF THE INVENTION

Vascular grafts include a wide variety of natural and synthetic tubular structures that may or may not contain valves. Valves in these tubular structures are usually intended to direct the flow of blood (or other nutrient materials) in one direction by preventing the backward flow of this (these) liquid solution(s). Examples of valved tubular structures include aortic, pulmonary, and mitral valves present in the hearts of most vertebrate animals and veins used to return blood flow from the periphery of the body to the heart for recirculation.

Vascular grafts constructed of synthetic materials include devices constructed from man-made polymers, notably Dacron and Teflon in both knitted and woven configurations such as those marketed by W.L. Gore, Inc. and Impra, Inc. where various forms of polytetrafluoroethylene (PTFE) are molded into a wide array of tubule structures (see for example U.S. Pat. Nos. 4,313,231; 4,927,676; and 4,655, 769.

Natural vascular grafts, taken in the context of the invention, include valved and non-valved tubular structures obtained by methodologies broadly classified under the term "tissue engineering". Notably, tissue engineered blood vessels such as described in U.S. Pat. Nos. 4,539,716, 4,546, 500, 4,835,102, and blood vessels derived from animal or human donors such as described in U.S. Pat. Nos. 4,776,853, 5,558,875, 5,855,617, 5,843,181, 5,843,180, and a pending patent application entitled "A Process for Decellularizing Soft-Tissue Engineered Medical Implants" (patent application Ser. No. 09/528,371 incorporated herein in its entirety). The present invention involves vascular grafts derived using a novel process associated with tissue engineering as well as a novel bioreactor device for use in the process.

Tissue engineered natural vascular grafts, hereinafter vascular grafts, can be manufactured by processing of natural vascular grafts (including for example, veins, arteries, and heart valves.) with the objective of removing the cellular elements without damaging the matrix structure of that tissue-a "reductionist" approach. This approach is generally referred to as decellularization and is the subject of several patents, of which U.S. Pat. No. 4,801,299 by Brendel and Duhamel is considered as one of the earliest such patents, and pending patent applications as described above. Decellularization of tissues has been attempted by incubating tissues in the presence of detergents, both anionic and nonionic, with and without digestion of nucleic acids.

Tissue engineered natural vascular grafts have also been constructed using a "constructionist" approach. This approach involves the extraction of natural cellular and matrix components to obtain purified (or partially purified) fractions and then using these fractions to reconstruct a vascular graft from individual components. Alternatively, specific components of a vascular graft, for example collagen(s), can be obtained using recombinant DNA technologies and such highly purified and homogeneous materials used in the construction of natural vascular grafts via tissue engineering. Methods and materials for 3-dimensional cultures of mammalian cells are known in the art. See, U.S. Pat. No. 5,266,480. Typically, a scaffold is used in a bioreactor growth chamber to support a 3-dimensional culture. The scaffold can be made of any porous, tissue culture compatible material(s) into which cultured mammalian cells can enter and attach.

Both the reductionist and constructionist approaches are attempts to provide an acellular matrix that can be used directly as an acellular graft.

The invention provides a bioreactor approach to reseeding of vascular grafts, such as a decellularized aortic heart valve. The approach involves removal of the basement membrane by enzymatic digestion. This removal of basement membrane is followed by pressure-differential induced movement of fibroblastic cells in a solution into the matrix structure and reendothelialization by incorporation of endothelial cells into a collagenous/noncollagenous solution. This latter solution is compacted, as necessary, by "pressure" binding of this mixture onto the luminal surface to recreate a "basement membrane" containing endothelial cells. Cells are induced to resume metabolic activities following treatment with specific growth factors, for example fibroblast growth factor, or platelet aggregation under a pulsatile flow of nutrient solutions. The novel design of the bioreactor facilitates the processes described in the present invention.

SUMMARY OF THE INVENTION

According to one aspect of the present invention, a device and process is described for recellularizing and reendothelializing essentially acellular or devitalized tissue grafts including vascular grafts for use in replacement of defective tissues including for example defective heart valves and vascular conduits. The device is a bioreactor designed to facilitate selected steps in the processing such as recellularization and reendothelialization. The process includes several steps which may be conducted outside of the bioreactor and several steps which may be conducted inside of the bioreactor such that most of the invention is carried out in a closed processing system that will dramatically restrict contamination by microbiological and chemical/biological elements. The process comprises the following steps:

1) use of an essentially acellular vascular graft, such as a heart valve, whether constructed as an acellular graft using tissue engineering methods or decellularizing a native vascular graft using methods known in the art;
2) attaching the acellular graft into the bioreactor by attaching the graft directly to the inlet and outlet port connections or by sewing/attaching the graft to sewing rings and attaching the sewing rings to the inlet and outlet port connections and closing the unit as illustrated in the attached figures;
3) optionally treating the acellular graft with various growth and/or differentiation factors, such as fibroblast growth factor (FGF), polylysine, hyaluronins, proteoglycans, RGD-containing peptides, sodium dodecylsulfate, or suramin, to achieve binding in the tissue matrix;
4) washing the acellular graft with an appropriate aqueous solution to remove unbound, or loosely bound growth and/or differentiation factors;

5) debriding the basement membrane using proteolytic enzymes, for example dispase and/or collagenase, to achieve total or partial removal of the basement membrane lining the luminal surface of the acellular graft;

6) washing the acellular graft with an appropriate aqueous solution to remove excess proteolytic enzymes;

7) seeding the acellular graft with a fibroblastic cell population, allogenously or autogenously derived, using a positive pressure mediated infusion of cells into the tissue matrix spaces;

8) washing the recellularized graft with an appropriate iso-osmotic solution such that only the luminal volume and the volume outside of the vascular graft are replaced and no additional pressure flow occurs across the matrix of the recellularized graft;

9) seeding the recellularized graft with an endothelial cell population, allogenously or autogenously derived, using a viscous collagenous/noncollagenous mixture containing the endothelial cells;

10) partially pressurizing the luminal volume to compress the viscous collagenous/noncollagenous/endothelial cell mixture onto the luminal surface of the now recellularized and reendothelialized graft;

11) washing the now recellularized and reendothelialized graft to remove excess viscous collagenous mixture;

12) applying a slow pulsatile flow of nutrient rich and growth factor containing medium, optionally containing allogenous or autogenous platelets, to establish a functionally viable cell population in the graft such that the fibroblastic cell population and the endothelial cell population establish a viable vascular graft;

13) applying a pulsatile flow of nutrient rich medium at a flow rate appropriate to provide a stress field in the tissue graft appropriate to the physiological stimulation of the cell population in that tissue graft;

14) Preserving the now recellularized and reendothelialized graft by methods know in the art of cryopreservation, cold-storage preservation, and/or nutrient-culture preservation, or directly shipping and implanting the graft post recellularizing/reendothializing.

BRIEF DESCRIPTION OF THE DRAWINGS

Preferred embodiments of the invention are shown in the drawings, wherein.

DETAILED DESCRIPTION OF THE PREFERRED EMBODIMENTS

Definitions

As used herein, "recellularization" means the repopulation of the matrix volume of a tissue engineered or devitalized tissue or decellularized-acellular matrix structure with a viable cell population that is either the desired cell phenotype and/or genotype or that which can be caused to differentiate into the desired cell phenotype and/or genotype.

As used herein, "reendothelialization means the repopulation of the flow surface of a tissue engineered or devitalized tissue or decellularized-acellular matrix structure with a viable endothelial cell population that is either phenotypically and/or genotypically an endothelial cell at the time of repopulation or that which can be caused to differentiate into the desired cell phenotype and/or genotype.

As used herein, "decellularization" means the removal of cells and cell remnants from a tissue matrix structure using liquid solution processing.

As used herein, "devitalized tissue" means a tissue having as it's major components collagens and elastin in the form of extracellular matrix from which has been removed cellular membranes, nucleic acids, and lipids, but retaining large molecular weight cytoplasmic proteins. These residual high molecular weight cytoplasmic proteins promote recellularization.

As used herein, "cell to cell communication" means the chemical and/or physical signaling between one or more cells and/or cell populations such that a given cell or cell population is stimulated to function in a manner necessary to the role of that cell in maintaining tissue function. This cell to cell communication can occur by paracrine types of signaling using large and small molecular weight factors and is generally restricted to within the tissue comprising the functional entity being observed or studied.

Unless otherwise defined, all technical and scientific terms used herein have the same meaning as commonly understood by one skilled in the art of tissue processing and cell culturing techniques. Although materials and methods similar or equivalent to those described herein can be used in the practice or testing of the invention, the preferred methods and materials are described below. All publications, patent applications, patents and other references mentioned herein are incorporated by reference. In addition, the materials, methods, and examples are illustrative only and not intended to be limiting.

Figure 1:
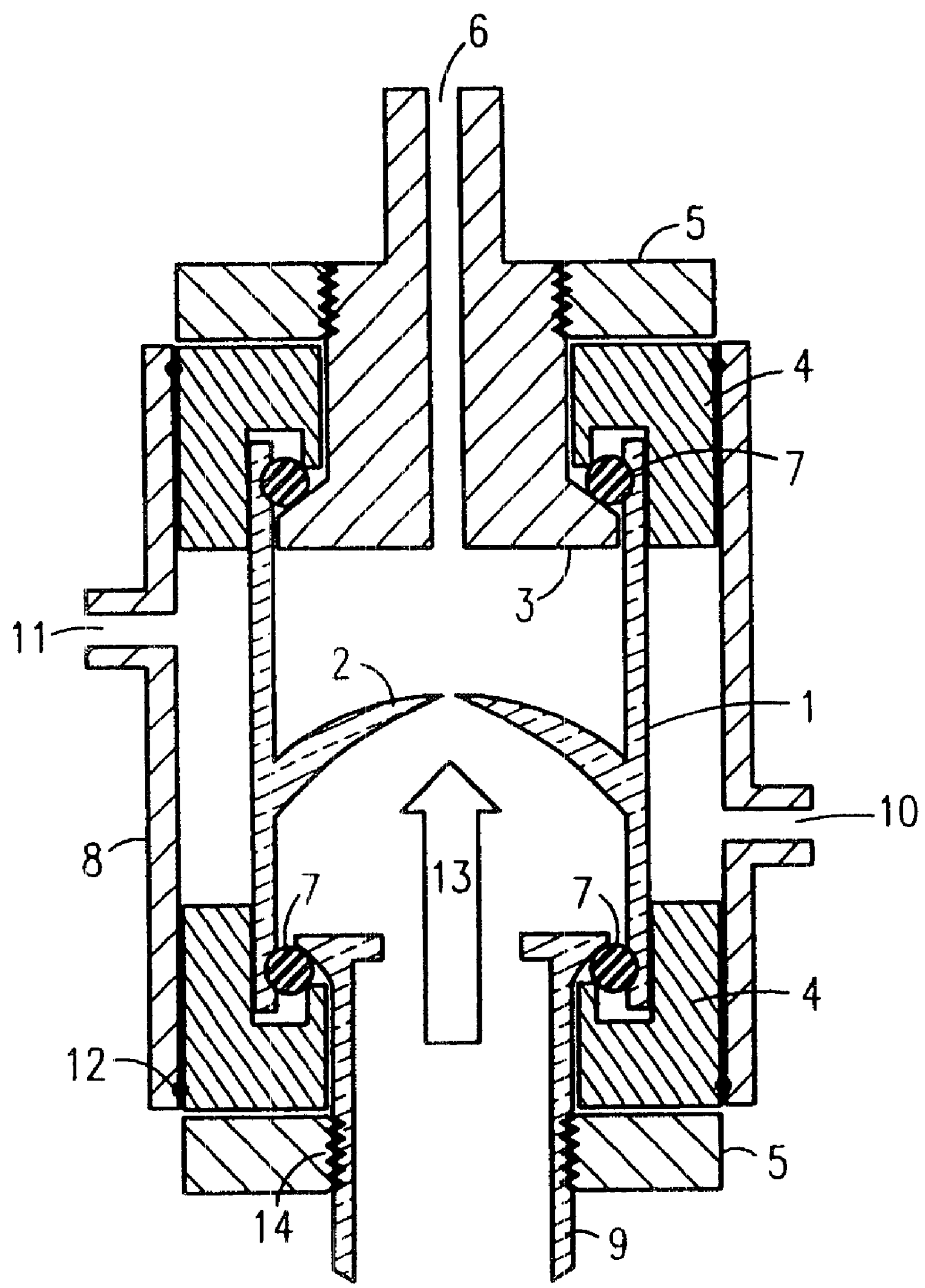
FIG. 1 is a view of one embodiment of the bioreactor showing a heart valve (1) held between inlet (9 and 4) and outlet (3 and 4) end plates and contained with in a clear jacket (8) designed to permit washing of the luminal side and adventitial side of the heart valve. This view does not provide details of the inlet end plate, of which one embodiment is provided in FIG. 2. Also shown is a view of one embodiment of the clamping device (7, 4, and 3 and 7, 4, and 9) used to hold the heart valve ends in the clamping ends of the inlet and outlet end plates. Tightening of the knurled nuts (5) as illustrated in FIG. 1 will draw the angled O-ring plates together forcing the O-ring out creating a tight hold on the end of a heart valve against the inside wall of the outer wall of the end plate. This type of clamping mechanism is known in the art of chromatographic columns and is not claimed in the present patent application. The flow of solutions is shown as arrow (13). The jacket (8) is shown having portals (10 and 11) that are in communication with pulse-dampening chamber (26) that is shown in FIG. 13.
Figure 2:
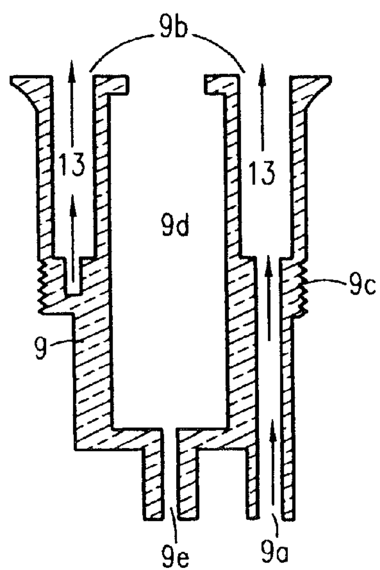
FIG. 2 is a view of one embodiment of the inlet end plate (9) presented to illustrate the chamber of end plate (9*d*) and the positioning of an inflatable piston at zero pressure with associated inlet for pressurized gas (9*e*) and an inlet port (9*a*) through which solutions and cells can be introduced that will exit through a circumferential opening (9*b*) into the luminal volume of the tissue being processed. The threads (9*c*) associated with this embodiment of the inlet end plate will be used in association with the knurled nut (FIG. 1 item 5) to tighten the end plate such that the tissue to be processed will be held tightly to the end plate.
Figure 3:
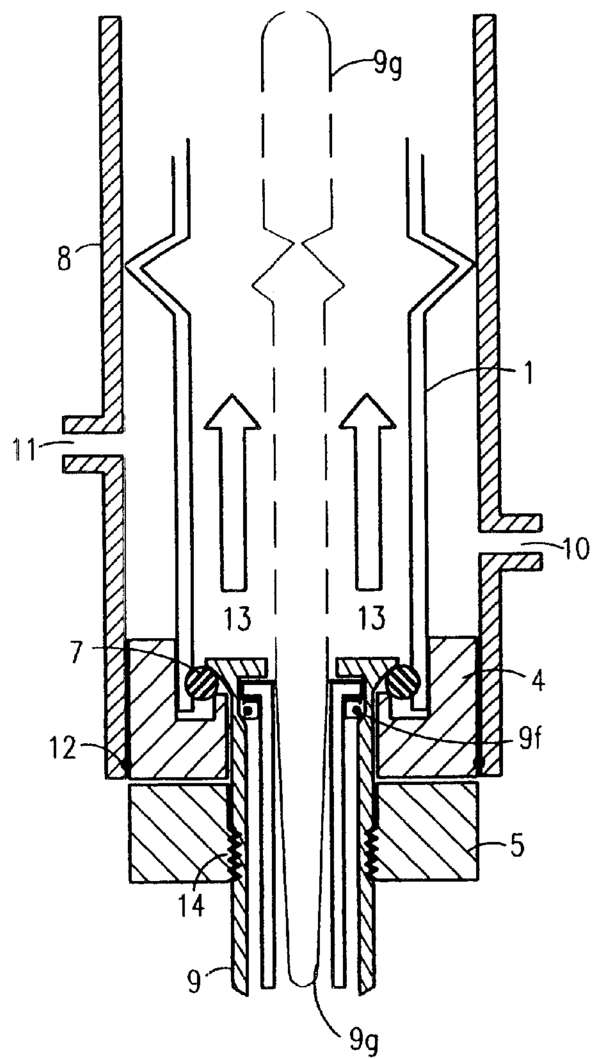
FIG. 3 is a view of one embodiment of the inlet end plate (4, 9, and 5) and one end of the bioreactor clear jacket (8) showing the position of the inflatable piston (9*g*) at some minimal pressure. The view is provided to illustrate the differences in solution volumes that can be present in the lumin of a heart valve (1) contained in the bioreactor during various stages of the processing where it is desired to control the volumes of processing solutions. As illustrated in the dashed line the inflatable piston (9*g*) will extend into the luminal volume of the tissue allowing change in volumes of solution(s) in the luminal space of that tissue. A small "O-" ring (9*f*) is used to retain the open end of the inflatable piston when placed into this end-plate component (9). The inflatable piston (9*g*) in this case is a variable length inflatable tube closed at one end such that the tube may be adjusted for length by cutting at the non-closed end and the non-closed end expanded over the piston shaft and held using any suitable clamping mechanism, for example an expandable O-ring (9*f*). The piston shaft is then inserted into the inlet end plate (9) and the knurled nut (FIG. 1 item 5) used to close the end-plate to the vein/artery segment. The inflatable piston may be inflated using "air" pressure applied at the air pressure inlet (9*e*, FIG. 2) such that the air moves into the pressure chamber forcing the inflatable piston out of the piston shaft and into the lumen of the artery/vein segment.
Figure 4:
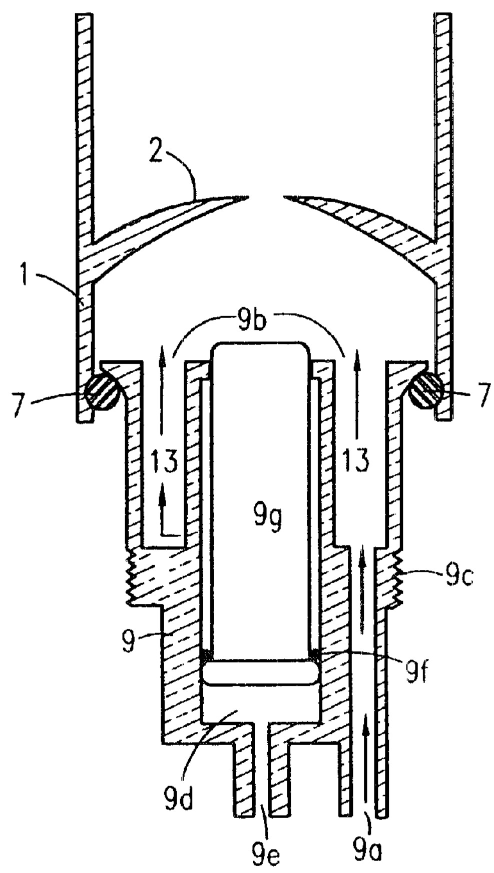
FIG. 4 is a view of one embodiment of the inlet end plate (9) showing the position of the inflatable piston (9*g*) at some pressure greater than minimal pressure in a chamber of end plate (9*d*). The view is provided to illustrate the differences in solution volumes that can be present in the lumin of a heart valve (1) contained in the bioreactor during various stages of the processing where it is desired to control the volumes of processing solutions. The inflatable piston is "sealed" using "O-" rings (9*f*) which allow the inflatable piston to move against the inside walls of chamber (9*d*) of inlet end plate (9). Processing solutions enter via inlet port (9*a*) and pressure to "air" inflate the inflatable piston enter via inlet port (9*e*). Threads (9*c*) are used to tighten the knurled nut (FIG. 1 item 5) to this component of the complete end plate.

The bioreactor used in this invention is intended to be used as a closed system to restrict contamination of the vascular grafts material(s) being processed. One of the preferred embodiments of the bioreactor is illustrated in FIG. 1 with details of the inlet end plate illustrated in FIG. 2. The dimensions of the bioreactor can be scaled to accommodate the tissue being processed where the inside diameter of the vascular graft can range between about 3–6 mm (for a small vein or artery graft substitute to as large as 28–35 mm for a pulmonary or aortic heart valve substitute. The essential dimensions are related to the need to allow for expansion of the graft being processed under a maximally anticipated pressure, for example 180 to 200 mm Hg for a valved or non-valved aortic conduit, such that the outside dimension of the graft does not come in contact with the inside wall of the jacket of the bioreactor. Similarly, the essential dimension of the inflatable piston should be such that during some minimal processing pressure, for example about 30 mm Hg for a valved or non-valved aortic conduit, the inside lumin (wall) of the graft does not come in contact with the outside dimension of the inflatable piston. Similarly, the graft holding O-ring mechanism must be small enough to allow the graft to be positioned up and over the O-ring such than a small suture line can be used to secure the graft prior to expansion of the O-ring gripping mechanism, if desired, yet small enough to allow the O-ring gripping mechanism to firmly pinch and hold the graft onto the inlet and outlet end plates. Optionally, fibrin glues, or similar such biologically compatible glues, can be used to secure a leak-proof seal of the vascular tissue to the device. The inlet port on the inlet end plate must be of sufficient inside diameter to allow a physiological flow rate of processing solutions, yet provide for an even distribution of fluid flow into the luminal volume of the graft being processed. The outlet port of the outlet port plate must be of sufficient inside diameter to allow a physiological flow rate of processing solutions to exit the bioreactor. The inlet and outlet ports of the jacket of the bioreactor should be of a large enough inside diameter to permit the inflow of solutions without creating turbulence on the adventitial side of the graft being processed. The means of creating these dimensions should be known to someone skilled in the art of manufacturing and the means of manufacturing are not claimed within the context of this invention. The materials comprising the bioreactor should be sterilizable using industry standards and could consist of solvent and heat resistant organic polymers manufactured by an injection molding process or of a metallic material manufactured by standard milling processes. Ideally, the bioreactor would be a disposable, single-use, device, but its design and construction would accommodate being taken apart, cleaned, reassembled, and sterilized prior to reuse.

Figure 5:
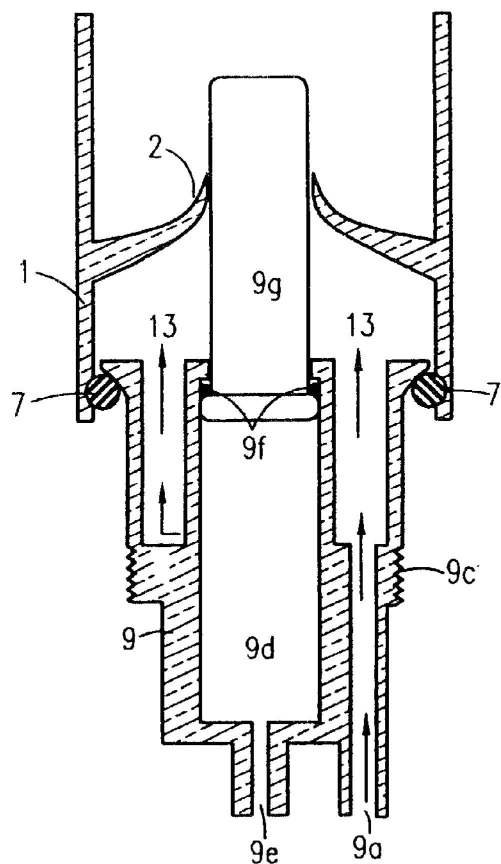
FIG. 5 is a view of one embodiment of the inlet end plate (9) showing the position of the inflatable piston (9*g*) where the bioreactor device is to be used to recellularize long artery and vein segments. The inflatable piston in this case is a variable length inflatable tube closed at one end such that the tube can be adjusted for length by cutting at the non-closed end and the non-closed end expanded over the piston shaft and held using any suitable clamping mechanism, for example an expandable O-ring (9*f*). The piston shaft is then inserted into the inlet end plate and the knurled nut (FIG. 1 item 5) used to close the end-plate to vein/artery segment. The inflatable piston can be inflated using "air" pressure applied at the air pressure inlet (9*e*, FIG. 2) such that the air moves into the pressure chamber forcing the inflatable piston out of the piston shaft and into the lumen of the artery/vein segment. The view is provided to illustrate the differences in solution volumes that may be present in the lumen of a heart valve (1), extending through valve leaflets, contained in the bioreactor during various stages of the processing where it is desired to control the volumes of processing solutions. In this figure the volume in the lumen of the heart valve is less than that illustrated in FIG. 4. The inflatable piston is "sealed" using "O-" rings (9*f*) which allow the inflatable piston to move against the inside walls of chamber (9*d*), illustrating formation of a tight seal at the end of chamber (9*d*). Threads (9*c*) are used to tighten the knurled nut (FIG. 1 item 5) to this component of the complete end plate.
Figure 6:
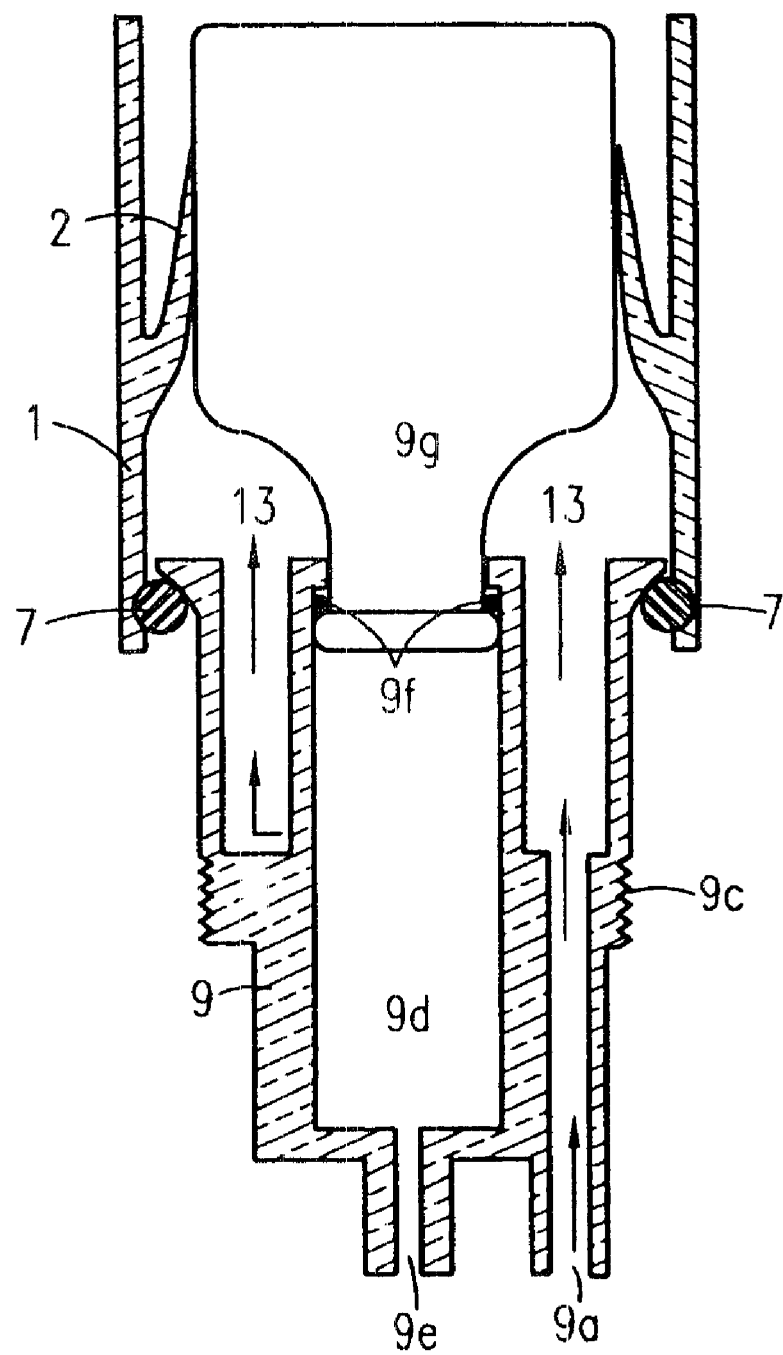
FIG. 6 is a view of one embodiment of the inlet end plate (9) showing the position of the inflatable piston (9*g*) at some pressure in the chamber of end plate (9*d*) sufficient to cause the piston to move into the lumen of the heart valve (1) and extend through valve leaflets. This pressure is sufficient to cause the piston to extend and to be inflated to a position where the outside walls of the inflatable piston almost touch (or touch) the inside wall of the heart valve (1). The view is provided to illustrate the differences in solution volumes that may be present in the lumen of a heart valve (1) contained in the bioreactor during various stages of the processing where it is desired to control the volumes of processing solutions. In this figure, the volume in the lumen of the heart valve is less than that illustrated in FIG. 5. The inflatable piston is "sealed", using "O-" rings (9*f*), which allow the inflatable piston to move against the inside walls of chamber (9*d*) illustrating formation of a tight seal at the end of chamber (9*d*). Processing solutions enter via inlet port (9*a*) and pressure to "air" inflate the inflatable piston enter via inlet port (9*e*). Threads (9*c*) are used to tighten the knurled nut (FIG. 1 item 5) to this component of the complete end plate.
Figure 7:
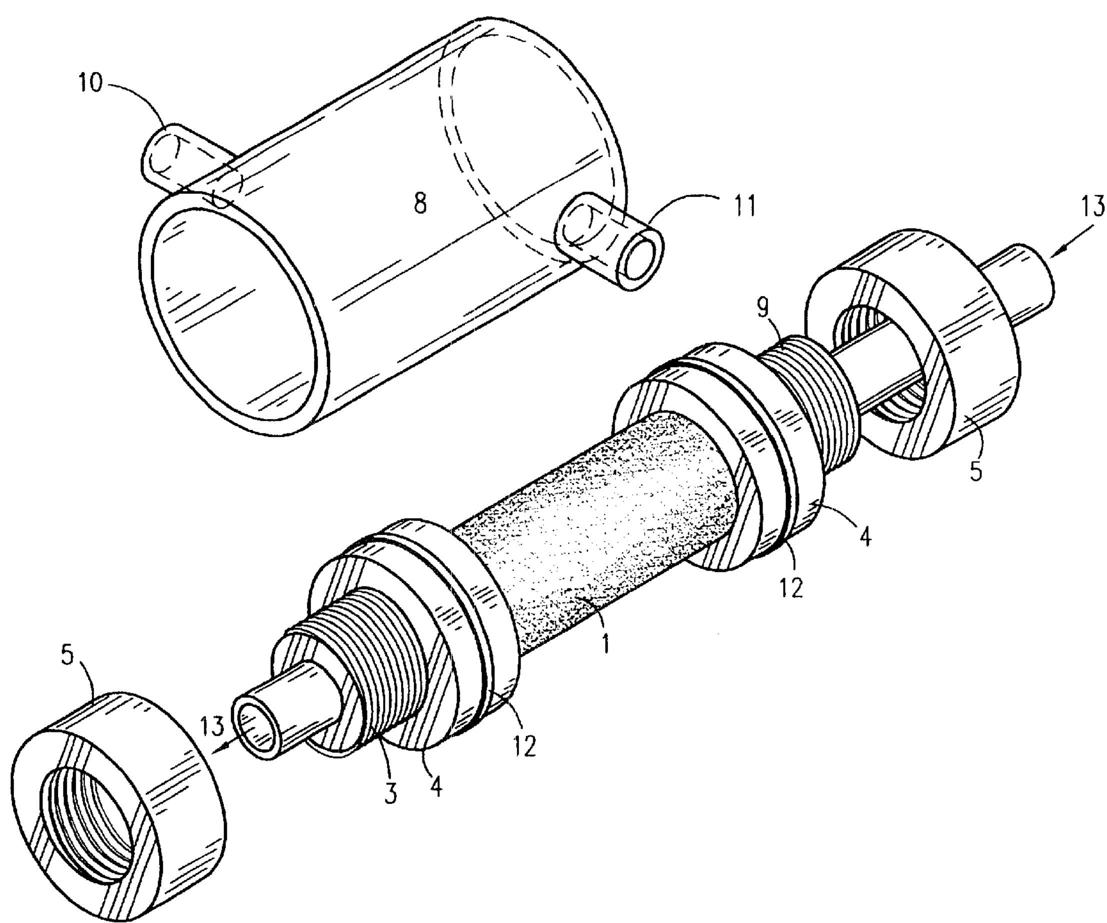
FIG. 7 is one illustration of an "exploded" view of the bioreactor showing the tissue to be processed (1) attached to the inlet and outlet end plates (4) (not differentiated in this illustration). Inlet and outlet ports (3 and 9) (not differentiated in this illustration) are tightened to hold the tissue using knurled nuts (5). The "O-" rings (12) used to seal the clear jacket (8) are of sufficient dimension as to allow sliding of the clear jacket over the outsides of the endplates during final assembly permitting positioning of the clear jacket inlet and outlet ports (10 & 11) to clear the end plates.
Figure 8:
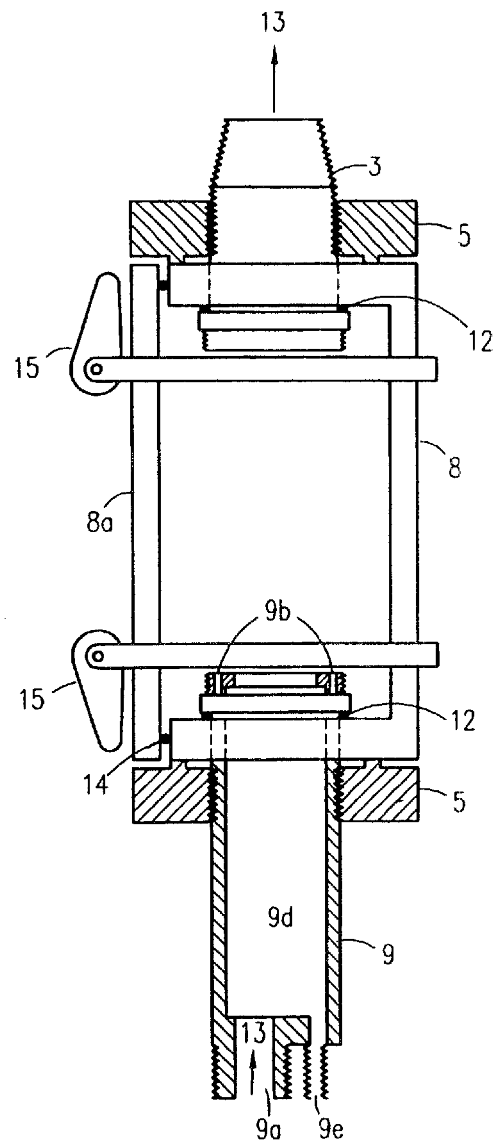
FIG. 8 is a view (side view) of a second embodiment of the bioreactor where the chamber of the bioreactor (8) consists of a, preferably, clear 5 sided rectangular box with inlet (9) and outlet (3) end plates in the long ends. In this embodiment, the inlet and outlet ports include an inlet endplate that consists of long flow tube that includes a chamber for the inflatable piston (9*d*) with the long flow tube locked into the end of the bioreactor using a knurled nut (5) and sealing "O-" rings (12). The outlet endplate (3) is shorter than the inlet endplate and also consists of a hollow tube sealed into the end of the bioreactor using a knurled nut (5) and "O-" rings (12) to seal the outlet port to the long end of the bioreactor. The "lid" (8*a*) of the bioreactor is sealed to the bioreactor using clamps (15) and a large "O-" ring (14) that fits in a grove around the top side of the bioreactor box. Inlet and outlet ports within the side-walls of the bioreactor for use in washing the adventitial side of the tissues and for allowing pressure outside tissues being processed to pulse to a pulse dampener are not visible in the present side view.
Figure 9:
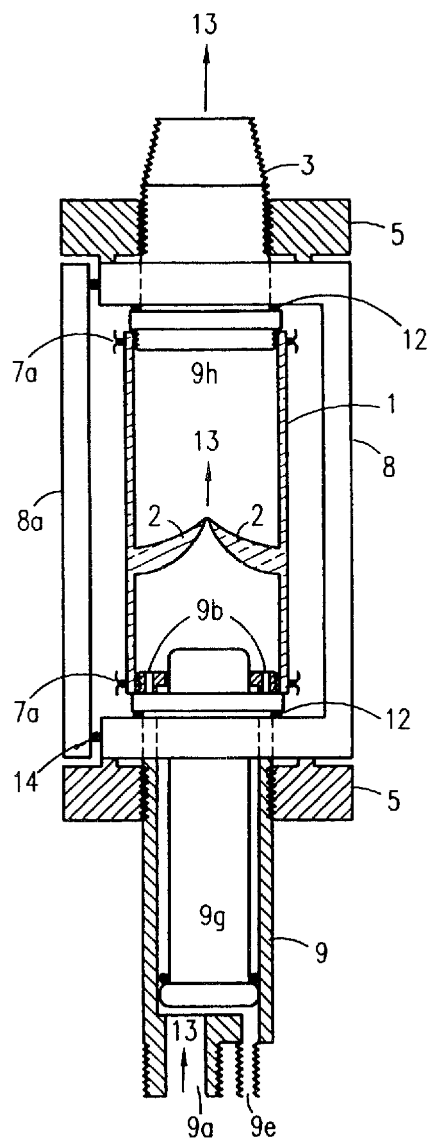
FIG. 9 is a second view (side view) of a second embodiment of the bioreactor showing an aortic valve (1) and an inflatable piston (9*g*) where the tissue is attached to the inlet (9) and outlet ports (3) using simple sutures (7*a*) to tie the tissue to the ridged ends on the inlet and outlet ports. In this illustration, the inflatable piston remains positioned in the chamber of the inlet port such that processing solutions may enter via (9*a*) and exit into the lumen of the valve at (9*b*). All other attributes of the illustration are as described in FIG. 8.
Figure 10:
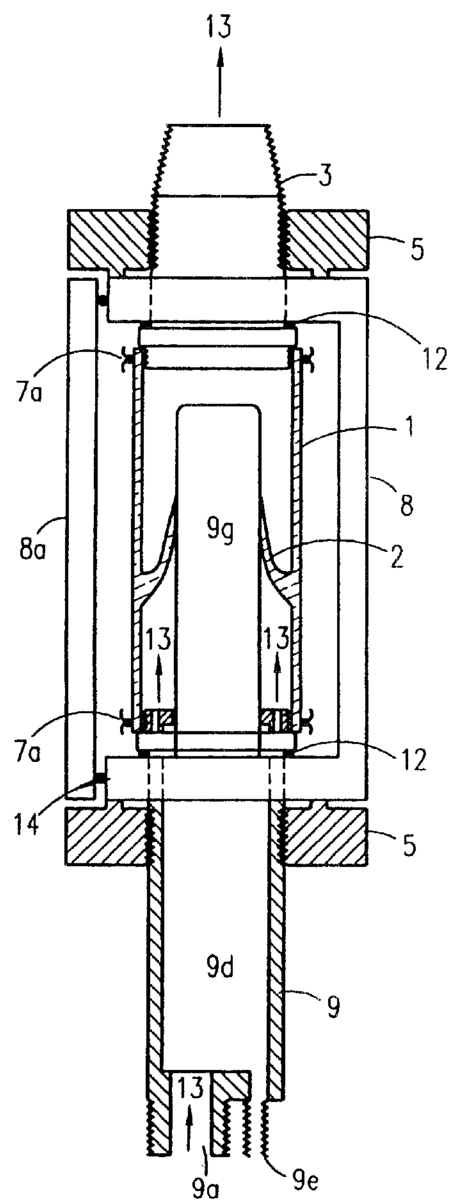
FIG. 10 is a second view (side view) of a second embodiment of the bioreactor showing an aortic valve (1) where the inflatable piston (9*g*) has been caused to enter the lumen of the valve using minimal pressure entering via inlet (9*e*). All other attributes of the illustration are as described in FIG. 8.
Figure 11:
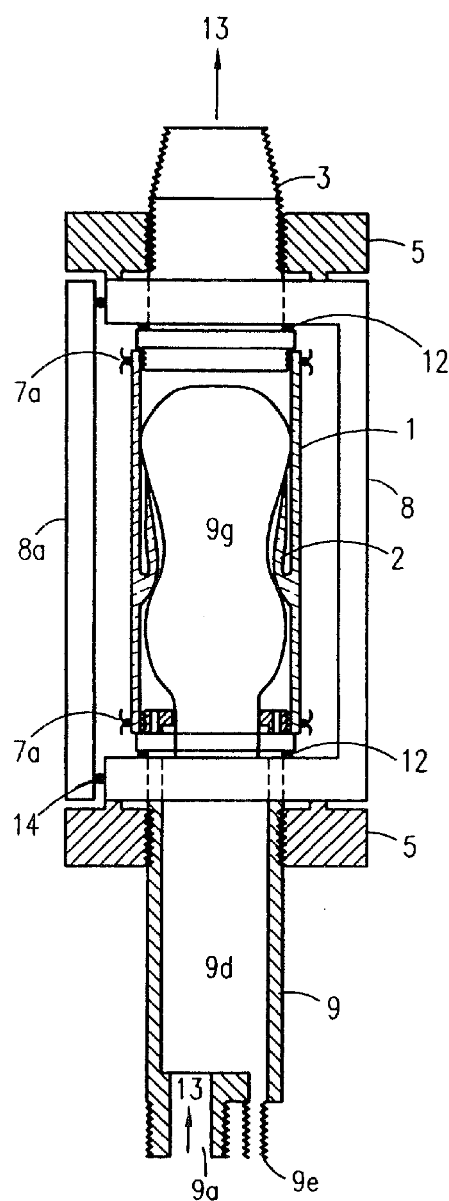
FIG. 11 is a second view (side view) of a second embodiment of the bioreactor showing an aortic valve (1) where the inflatable piston (2) has been caused to enter the lumen of the valve and inflated to approach the basement membrane (lumen side) of the valve using greater than minimal pressure entering via inlet (9*e*). All other attributes of the illustration are as described in FIG. 8.
Figure 12:
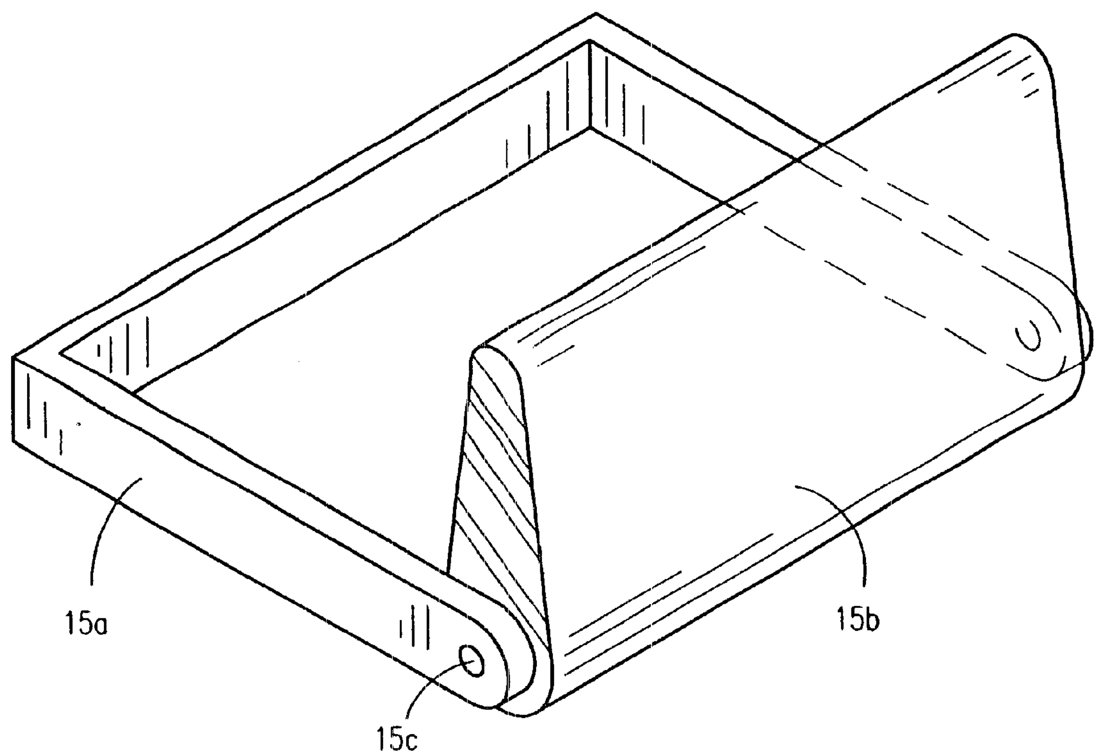
FIG. 12 is a view of the clamping device (15) used to affect closure of the bioreactor illustrated in FIG. 8, a second embodiment of the bioreactor. The position of the pin (15*c*) on the locking flange (15*b*) is off-center to allow compression of the top of the bioreactor to the body of the bioreactor as illustrated in FIG. 8 using loop (15*a*) (clamp closest to the inlet port is open and clamp closest to the outlet port is closed).
Figure 13:
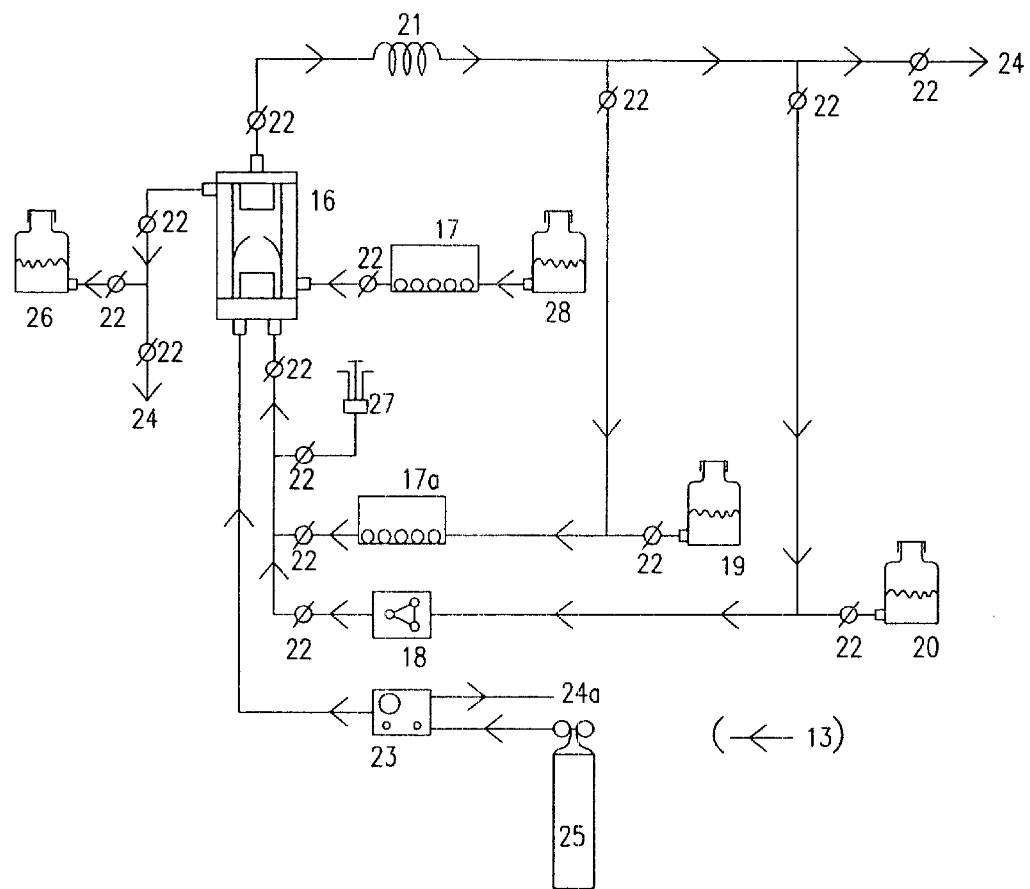
FIG. 13 is a view of the embodiment of a flow diagram provided to illustrate how the flow of various processing solutions are directed to the bioreactor. This flow, using valves (22), peristaltic (17) and pulsatile pumps (18), in-line filters (not shown), solution reservoirs (19, 20, and 28), waste containers (24), and flow restricters (21) is indicted using arrows (13). Enzymes and reagents may be injected into the bioreactor (16) using the "syringe" inlet port (27). The solutions in reservoir (28) may be pumped, using a peristaltic pump (17), into the bioreactor volume outside the luminal volume of the tissue being processed exiting to the pulse-dampening chamber (26) or to waste (24). The solutions in reservoir (19) may be pumped, using a peristaltic pump (17*a*) into the luminal volume of the tissue being processed exiting to the flow restricter (21) being recycled via the flow diagram illustrated (returning to the peristaltic pump (17*a*)) or exiting to waste (24). For tissue conditioning, pulsative flow rates may be achieved through the graft lumen using the pulsatile pump (18), pumping solutions from reservoir (20) with such solutions being directed to waste (24) or recycled via the flow route indicated as returning to the pulsatile pump. For pulsatile pumping and graft conditioning a flow restrictor will be added to permit flow of greater fluid volumes. The pressurized gas (25) will be used to inflate the inflatable piston component of the bioreactor using pressure regulator (23) and the inflatable piston deflated via exit port (24*a*).

The Process of recellularization and reendothelialization of a vascular graft, for example an aortic heart valve as described herein, can be described in general terms. The vascular graft is procured from a human or animal source and transported to the processing facility in a hypotonic solution, in a sterile bag, on wet ice. Once at the processing facility the tissue would be trimmed of excess muscle and fat, the proximal and distal ends cut smoothly perpendicular to the long axis of the tissue and/or optionally attaching to sewing rings, and mounted into the tissue holding O-ring constraints on the inlet (1) and outlet (2) end plates (as illustrated in FIG. 1 and FIG. 5). The jacket (3) would be applied and the graft extended to its natural length. If the tissue is an aortic heart valve, proper alignment of the vascular tissue could be checked for valve compliance by filling the outflow side of the valve (using the outflow port (4) of the outlet end plate (2) (distal to blood flow) and observing for leaks past the valve leaflets. A compliant valve should not leak. The bioreactor can then be attached to its inlet (5) and outlet lines (6) that are already attached to the various solvent containers (7 and 8) and waste containers as illustrated in FIG. 6. Subsequent processing is divided into separate phases for purposes of description herein, however, the process is intended to be continuous and incorporating each described part of the overall process.

Decellularization: If the tissue has not already been decellularized, or was not acellular following construction, the inflatable piston is caused to enter into the luminal volume of the tissue and inflated to approximately fill the luminal volume. A HEPES buffered (pH 6.0 to 7.5) hypotonic solution of non-ionic detergent(s), for example polyoxyethylene alcohol sold under the trademark BRIJ-35™ at 0.2 to 1.0 mM, preferably containing the commercially available recombinant endonuclease sold under the trademark BENZONASE™ by EM industries, or other suitable enzyme preparations of DNase and RNase, is pumped into the luminal space of the graft through the inlet port of the inlet end plate and into the volume between the adventitial side of the graft and the jacket through the inlet port of the jacket. These fluids are allowed to exit the bioreactor via the outlet port in the jacket and the outlet port of the outlet end plate, returning to the peristaltic pump (9) for recirculation back into the bioreactor. In-line filters can optionally be used to remove particulate materials from the circulating solution, and this recirculation of decellularization solution is allowed to proceed for between three (3) and twelve (12) hours at temperatures between 20° C. and 37° C. Decellularization can be monitored at 260 nm for degradation products of the nucleic acids present in the cells being solubilized and degradation of cellular macromolecules. Ideally, the flow rates of decellularization solutions will be maintained such that a slight positive pressure exists in the luminal volume of the tissue being decellularized.

Washing: When decellularization has been completed, the decellularization solution is washed from the bioreactor, tissue, and tubing by switching processing solutions to preferably ultrapure water, however various buffered salt solutions, made hypotonic or hypertonic, may be substituted as required to remove residual cellular elements, and diverting the effluent solution flow to waste. Washing volumes need to involve volumes in excess of 10 volume changes of the bioreactor volume.

Treatment: The treatment phase of the process is optional, but desirable. The treatment phase of the process involves recirculation flow of aqueous solutions into, through and around the tissue in the bioreactor. This recirculation flow involves flow of solutions through both the luminal and adventitial (i.e. volume between the adventitial surface of the tissue and the jacket) volumes.

Treatment solutions, for purposes of this specific process include low ionic strength HEPES (or similar Good buffer) buffered (pH 6.5–7.4) aqueous solutions of fibroblast growth factor (0.1 nM to 0.1 $\mu$M), suramin (0.001% to 1.0% by weight), sodium dodecylsulfate (0.001% to 1.0% by weight), bone morphogenetic protein(s) 1, 2, 6, and 7 (0.01 nM to 0.1 $\mu$M), aggrecan (0.0001% to 0.01% by weight), hyaluronins (0.0001% to 0.1% by weight), interleukin 6 (0.001 nM to 0.1 nM), glutathione ethylester (or glutathionine), and/or transferin. Recirculation volumes may be minimized by inserting and inflating the inflatable piston in the luminal volume of the graft.

Washing: When treatment has been completed, the treatment solution(s) is (are) washed from the bioreactor, tissue, and tubing by switching processing solutions to preferably ultrapure water, optionally supplemented with glutathione ethylester, however various buffered salt solutions or alcohol solutions may be substituted as required to remove residual cellular elements and treatment agents, and diverting the effluent solution flow to waste. Washing volumes need to involve volumes in excess of 10 volume changes of the bioreactor volume.

Basement Membrane Removal/Perforation: With the inflatable piston in the inflated position, buffered solutions of proteolytic and/or hydrolytic enzymes can be injected through the sample inject (10) and pumped into the luminal volume of the tissue via the inlet port of the inlet end plate. During this process, the outlet port of the outlet end plate needs to be opened. When the volume present in the luminal volume of the tissue has been replaced by the proteolytic solution, the inlet port and outlet ports of the inlet and outlet end plates can be closed. For this step of the process, both the inlet and outlet ports of the jacket remain in the closed position. The proteolytic enzymes used in this step of the process include trypsin, chymotrypsin, elastase, collagenase, dispase, ficin, papain, and/or alkaline protease. The hydrolytic enzymes used in this step of the process include hyaluronidase, glucuronidase, and/or neuraminidase. The enzymes may be free in solution or attached to microscopic beads, such that hydrolysis of basis membrane will occur only where these microscopic beads, to which hydrolytic enzymes are tightly attached, come in physical contact with the basement membrane. See for example immobilized papain, pepsin, trypsin as attached to cross-linked 6%/14% beaded agarose and available from Pierce Chemical Company (product numbers 20341ZZ, 20343ZZ and 20233ZZ, respectively). Alternatively, specific bacterial species which produce and secrete specific hydrolytic enzymes, for example *Clostridium histolyticum* for collagenase, *Bacteroides gingivalis, Fusobacterium nucleatum, Actinobacillus actinomycetemcomitans,* and/or mammalian cells such as U937 monoblastoid cells, and/or an oral flagellate such as *Trichomonas tenax,* can be used instead of the microscopic beads (to which hydrolytic enzymes are attached) to digest holes in the basement membrane. This step in the process is intended to be of only sufficient time to permit digestion of a significant portion of the basement membrane (that membrane to which the endothelial cells attach in a native tissue) to allow penetration of the fibroblastic cell population into the matrix structure. The time intervals, enzymes, enzyme concentrations, and buffer conditions will be dictated by the type of graft being treated and the condition of the basement membrane of the tissue at the time of treatment. For example, for an aortic valve denuded of endothelial cells during the initial cold transport in hypotonic solutions, an appropriate enzyme concentration and time might include, but not be limited to, the enzyme collagenase at 0.01 IU/ml to 1.0 IU/ml for periods of time between 30 to 180 minutes. Times that can be expected to achieve the desired digestion of basement membrane in a typical aortic heart valve. For aortic valves retaining a significant endothelial cell layer, dispase (0.01 IU/ml to 0.5 IU/ml) may need to be added to the collagenase solution to help remove the endothelial cells permitting access of the collagenase to the basement membrane. Use of trypsin, chymotrypsin, elastase, ficin, papain, and/or alkaline protease can be used to enhance basement membrane digestion, however they can also be expected to degrade the underlying tissue matrix if incubation times are greater than 30 to 60 minutes. Incubation temperatures should be between 20° C. and 37° C. By regulating the size(s) of the microscopic beads, or bacterial species, it should be possible to not only control the size(s) of the holes created in the basement membrane, but to control the number of holes per unit surface area of the basement membrane by controlling the density of the microscopic beads (bacteria) used in the treatment solution.

Washing: It is essential that the proteolytic and hydrolytic digestion of the basement membrane be terminated quickly and efficiently. Towards this end, washing of the tissue to terminate removal of the basement membrane should be accomplished at reduced temperatures, for example 0° C. to 5° C., with rapid flow of buffered (pH 5.0 to 6.0) water solutions through both the luminal and adventitial volumes of the bioreactor. Flow of these washing solutions should be directed to waste. Wash volumes should be in excess of 20 bioreactor volumes over a time interval of 30 to 180 minutes.

Fibroblast Cell Seeding: Fibroblast cell seeding through the sample inject (10) (FIG. 6) of the tissue can be accomplished following removal of the basement membrane. To accomplish this cell seeding, either of two approaches may be used. In one approach, the inflatable piston is present in the luminal volume of the graft and in the second approach the inflatable piston is not present in the luminal volume of the graft. In both approaches, positive pressure will be used to induce movement of the fibroblast cells into the tissue matrix. The fundamental differences in how this positive pressure is applied constitutes the essential difference in the two approaches Approach number one: When the inflatable piston is present in the luminal volume of the graft, fibroblast cells (obtained from either primary tissue digests of the intended recipient of the graft (autograft cells) or from fibroblastic cells maintained in tissue culture (allograft cells)) will be pumped into the luminal volume of the graft via the inlet port of the inlet end plate. During the initial stages of delivery of the cells into this luminal volume, the outlet port of the outlet end plate will be open and the inlet and outlet ports of the jacket will be closed. The fibroblast cells will be at total viable cell numbers between $1\times10^6$ and $1\times10^8$ cells/tissue to be recellularized. The total number of cells to be infused into the matrix of a specific tissue will approximate 1000 to 10,000 cells/mm$^3$ of tissue matrix. Once the cells have been delivered into the luminal volume of the tissue, the outlet port of the outlet end plate can be closed and the outlet port of the jacket opened (with flow directed to waste). The flow rate on the peristaltic pump can be reduced to achieve a minimal positive pressure in the luminal volume of the tissue. Solution being pumped is switched from a cell suspension to a nutrient and growth factor-rich tissue culture medium supplemented with glutathione ethylester (or similar antioxidant) and/or similar anti-apoptotic agents such as IGF-1 or ZVAD-fmk (a caspase inhibitor), but not supplemented with serum. Flow of this nutrient solution is maintained for between 3 to 12 hours, or until cells can be detected in the outflow solution from the bioreactor, at 37° C. After about 12 hours, flow of nutrient is directed out of the luminal volume of the tissue via the outlet port of the outlet end plate to waste.

Approach number two: When the inflatable piston is not present in the luminal volume of the graft, fibroblast cells (obtained from either primary tissue digests of the intended recipient of the graft (autograft cells) or from fibroblastic cells maintained in tissue culture (allograft cells)) can be added via the sample inject (10) (FIG. 6) and pumped into the luminal volume of the graft via the inlet port of the inlet end plate. During the initial stages of delivery of the cells into this luminal volume, the outlet port of the outlet end plate will be open and the inlet and outlet ports of the jacket will be closed. The fibroblast cells will be at total viable cell numbers between $1\times10^6$ and $1\times10^8$ cells/tissue to be recellularized. The total number of cells to be infused into the matrix of a specific tissue will approximate 1000 to 10,000 cells/mm$^3$ of tissue matrix. Once the cells have been delivered into the luminal volume of the tissue, the outlet and inlet port of the outlet and inlet end plate can be closed and the outlet port of the jacket opened (with flow directed to waste). Pressure can be slowly applied to the inflatable piston to create a positive pressure in the luminal volume of the tissue sufficient to distend the tissue. As the cell suspension volume becomes less, additional pressure is applied to the inflatable pistons to maintain the positive pressure and flow of solution in the luminal volume to the adventitial side of the tissue. When it is determined that the cell volume has been significantly diminished and cells have penetrated into the matrix spaces, the inlet and outlet ports of the inlet and outlet end plates are opened, and nutrient solution not containing serum (as described above) is pumped into, through, and out of the bioreactor being directed to waste.

Reendothelialization of the Tissue: Following removal of the fibroblastic cell population from the luminal volume of the graft, endothelial cells are mixed into a viscous, collagenous/non-collagenous, solution at total cell numbers calculated as necessary to cover the luminal surface of the graft being reendothelialized. Such total cell numbers may be calculated by anyone skilled in the art and knowing the surface area typically covered by an endothelial cell in a native vascular graft. The collagenous/noncollagenous solution will include antioxidants such as glutathione ethylester in nutrient medium and collagen primarily of type IV, derived by extraction of tissues or as a recombinant product, however other collagen types (for example, types I, II, V, VII and X) may be included as desired. The concentration of collagen can range between about 0.1% and 2% by weight. The endothelial cells may be derived as primary cultures from the intended recipient of the tissue graft (an autograft approach) or from endothelial cell cultures derived from cell banks (an allograft approach) which may or may not have been genetically manipulated to reduce immunogenicity or improve paracrine functions. In that endothelial cells express MHC antigens, an allograft approach to seeding of enthothelial cells would not be expected to be retained on the luminal surface of a reendothelialized graft for extended periods of time post transplantation.

Endothelial cells present in a collagenous/noncollagenous solution are injected into the system via the sample inject (10) (FIG. 6) and pumped into the luminal volume of the tissue contained in the bioreactor via the inlet port of the inlet end plate. During this process, the outlet port of the outlet end plate is opened, and the inflatable piston is extended into the luminal volume of the tissue and inflated to a distance between 2 and 5 mm from the luminal surface of the tissue. The inlet and outlet ports of the jacket are closed during this step of the process. The viscous collagenous/noncollagenous mixture of endothelial cells is pumped into the volume between the tissue and the inflatable piston and the outlet and inlet ports of the outlet and inlet end plates are closed. Pressure is then slowly applied to the inflatable piston until the outside wall of the piston reaches the inside wall of the lumen of the tissue. If necessary, pressure can be released and reapplied as needed to evenly distribute the collagenous cell mixture evenly between the inflatable piston and the luminal surface of the tissue. At a specified point in this process, the increase in pressure with time is stopped and a pressure sufficient to maintain the piston wall in contact with the lumen wall is maintained for between 1 and 6 hours. The temperature during this process is maintained at 37° C. At the end of this incubation period, the inlet and outlet ports of the inlet and outlet end plates are opened and nutrient medium is slowly pumped into the luminal space of the tissue while the pressure on the inflatable piston is slowly reduced. The objective is to have the pressure induced flow of the nutrient medium begin to "peel" the inner luminal surface of the tissue from the inflatable piston at the "proximal end" of the tissue and to have this "peeling" process proceed towards the "distal end" of the tissue. Flow of nutrient medium through the luminal volume of the tissue should be slow and the eluent monitored for fragments of collagen/endothelial cells. If fragments appear in the eluent, the inflatable piston should be reinflated and incubation continued for a time period necessary to cause the collagen/endothelial cell mixture to adhere to the tissue.

The recellularized and reendothelialized tissue should be incubated at 37° C. for between 12 and 24 hours with a slow flow of nutrient and growth factor enriched HEPES buffered tissue culture medium supplemented with glutathione ethylester (or similar antioxidant), anti-apopotic agents such as, for example, IGF-1 and/or ZVAD-fmk (a caspase inactivator), fetal calf serum (or similar serum substitute if use of a serum-free medium is desired) and selenium/transferin as known to anyone skilled in the art of tissue culture additives. Flow rates can be determined by one skilled in the art of monitoring eluent medium for glucose, lactose, ammonia, etc., such that metabolic states of the cells can be determined and flow rates either increased or decreased according to nutrient depletion or waste product accumulation.

Graft Conditioning: Prior to transplantation, it may be desirable to precondition the graft by subjecting it to high pressure pulsatile flow of nutrient and growth factor enriched HEPES buffered tissue culture medium, at 37° C., supplemented glutathione ethylester (or similar antioxidant) and anti-apoptotic agents, for example IGF-1 and/or ZVAD-fmk (a caspase inactivator), with fetal calf serum (or similar serum substitute if use of a serum-free medium is desired) and selenium/transferin. The pressure and pulsatile flow patterns should be adjusted to simulate those pressures and pulsatile flow patterns to be found in the site in which the graft is to be implanted. The outlet port of the jacket should be open with flow of solution contained in the space between the tissue graft and the jacket directed to a pulse-dampening device to control the application of stress, and strain, to the graft. During this preconditioning, eluent solution should be monitored for fragments of collagen/endothelial cells. These will appear as particulate materials in the outflow side of the graft. Preconditioning times will vary with tissue graft type and desired alignment and orientation of the endothelial cells covering the luminal surface of the graft. Preconditioning is primarily directed at causing release of any collagen/endothelial cell fragments that will be release and to stimulating cell to cell interactions essential to long-term function and maintenance of a viable cell population in the tissue graft.

Cell Selection: Recellularization and reendothelialization of an acellular vascular graft can reasonably be expected to occur under the conditions described. However, it is important that the appropriate type of fibroblastic and endothelial cell population be selected for the recellularization/reendothelialization events. All cells, with the exception of reproductive cells such as eggs and sperm, are omnipotent, i.e. contain the same complement of genes and genetic material. However, some cells are more differentiated towards a given phenotype than other cells and there exists within fibroblastic cell populations in a body, fibroblastic cells with differing degrees of differentiation towards a specific phenotype. For example, there exist fibroblastic cells designated as myofibroblasts, based on tissue of origin, and these myofibroblasts may originate from aortic conduit tissue, myocardium, or similar contractile tissues. In that proper growth and differentiation factor mediated cell stimulation can be used to direct, or redirect, cell growth and differentiation, origin of a fibroblastic cell population to be used in recellularization of a cardiovascular tissue is less important than preventing triggering of a programmed cell death process commonly referred to as “apoptosis”. Morphologically, apoptosis is characterized by chromatic condensation, cell shrinkage, and membrane blebbing. Within the cell, various proteases and endonucleases are activated leading to degradation of protein and nucleic acids.

This is in contrast to the other mode of cell death, necrosis, which is uncontrolled in nature and is characterized by swelling and lysis of the cell. Oxidative stress is potentially a common signaling mechanism among diverse inducers of apoptosis and thus the inclusion of antioxidants or other agents such as IGF-1 and/or ZVAD-fmk (a caspase inactivator) in the processing and nutrient culture medium solutions described in this invention represents an important element of recellularization/reendothelialization designed to restrict programmed cell death in these tissues post-transplantation. Glutathione ethylester is a strong antioxidant that is freely permeable into cells. Although not claimed in this invention, it is theoretically possible to genetically manipulate cells used in repopulation of cardiovascular tissues by enhancing activity of genes acting as promoters (e.g. bax, Fas, and p53) and effectors (ICE-like proteases) or inhibitors (e.g. bcl-2, bcr-abl) of the process. Bcr-abl can be an activated form of a gene that is antiapoptotic.

Thus, although the present invention is not directed towards use of specific fibroblastic or endothelial cells derived from specific tissues, it is an important aspect of the present invention to use metabolically and reproductively viable cell populations and to include in the various nutrient and processing solutions, additives which enrich the metabolic functions of these cells and which serve to restrict induction of the process of apoptosis until the cell populations can be properly oriented and stimulated, both mechanically and chemically, to resume proper cell to cell communication essential to long-term viability and function. Initial stimulation of the endothelial cells used to construct a new basement membrane or fill the holes in the basement membrane formed from the microscopic bead containing hydrolytic enzymes can occur via addition of fibroblast growth factor into the nutrient medium. In addition, however, platelets from the intended recipient, or donor-derived platelets, can be used to treat the newly constructed basement membrane. Addition of platelets to the bioreactor following inflatable piston compression of the collagenous/noncollagenous/endothelial cells construct will result in platelet aggregation and activation by the “rough” protein structure. This platelet aggregation and activation will serve a similar purpose as addition of fibroblast growth factor to the nutrient medium, or preaddition to the construct, and will localize delivery of essential growth and differentiation factors at the site on the new basement membrane where it is desired to have a smooth layer of overlapping and function endothelial cells.

What is claimed:

1. A process for generating a transplantable recellularized and reendothelialized tissue graft, comprising:

harvesting tissue from a donor or producing tissue by tissue engineering methods;

eliminating native cells from said tissue to provide a tissue matrix;

removing basement membrane from a luminal surface of said tissue matrix;

treating said tissue matrix with factors to produce a treated tissue matrix;

recellularizing said treated tissue matrix with a fibroblastic or myofibroblastic cell population to produce a recellularized tissue matrix;

reendothelializing a luminal surface of said recellularized tissue matrix with an endothelial cell population to produce a repopulated tissue matrix; and preconditioning said repopulated tissue matrix to promote cell to cell communication, retard apoptotic events, and orient molecular structure of said repopulated tissue matrix to produce said transplantable recellularized and reendothelialized tissue graft.

2. The process of claim 1 wherein the tissue is a tubular structure.

3. The process of claim 2 wherein the tubular structure is an artery or vein.

4. The process of claim 2 wherein the tubular structure is a small intestine.

5. The process of claim 2 wherein the tubular structure is a urethra.

6. The process of claim 2 wherein the tubular structure is cellular or acellular.

7. The process of claim 1 wherein the tissue is an aortic or pulmonary heart valve.

8. The process of claim 7 wherein the heart valve is cellular or acellular at the time of processing.

9. The process of claim 1 wherein the tissue has been constructed using a tissue engineering process.

10. The process of claim 9 wherein the tissue engineered tissue is cellular or acellular.

11. The process of claim 1 wherein the tissue is derived from small intestine.

12. The process of claim 1 wherein the tissue is derived from connective tissue that has been made tubular.

13. The process of claim 1 wherein the tissue are derived from human donors.

14. The process of claim 1 wherein the tissue are derived from nonhuman donors.

15. The process of claim 1 wherein eliminating further comprises the use of detergents.

16. The process of claim 15, wherein the detergents comprise polyoxyethylene alcohol, polyoxyethylene p-t-octyl phenol, polyoxyethylene nonylphenol, polyoxyethylene sorbitol esters, or sodium lauryl sulfate.

17. The process of claim 15, wherein the detergents comprise polyoxyethylene alcohol.

18. The process of claim 17, wherein the concentration of polyoxyethylene alcohol is between 0.22 and 1.0 mM.

19. The process of claim 1 wherein eliminating further comprises the use of nuclease.

20. The process of claim 19 wherein the nuclease comprises DNase and RNase.

21. The process of claim 19 wherein the nuclease comprises endonuclease.

22. The process of claim 21, wherein the endonuclease degrades DNA and RNA.

23. The process of claim 22, wherein the endonuclease is derived by recombinant biology.

24. The process of claims 1, wherein the factors comprise fibroblast growth factor, endothelial growth factor, platelets, suramin, sodium dodecylsulfate, interleukin 6, bone morphogenetic protein, aggrecan, transferin, selenium, or hyaluronins.

25. The process of claim 1, wherein removing further comprises the use of enzymes.

26. The process of claim 25, wherein the enzymes are covalently attached to microscopic beads.

27. The process of claim 26, wherein the microscopic beads range between 5 microns to 500 microns in diameter.

28. The process of claim 26, wherein the microscopic beads are synthetic.

29. The process of claim 25, wherein the microscopic structures microorganisms.

30. The process of claim 29, wherein the microorganisms are selected from the group consisting of *Clostridium histolyticum, Bacterioides gingivalis, Fusobacterium nucleatum, Actinobacillus actinomycetencomitans,* U937 monoblastoid cells and *Trichomonas tenax.*

31. The process of claim 23 wherein the enzymes are selected from the group consisting of mouse T-cell specific serine proteinase 1, human leukocyte elastase, dispase, trypsin, chymotrypsin, papain, ficin, hyaluronidase, glucuronidase, elastase, mannase, and neuraminidase.

32. The process of claim 23, wherein the enzymes are not attached to microscopic beads.

33. The process of claim 1, wherein the fibroblastic or myofibroblastic cells are viable and derived from primary cultures derived from the individual receiving the tissue graft.

34. The process of claim 1, wherein the fibroblastic or myofibroblastic cells are viable and derived from cultures derived from an individual not receiving the tissue graft.

35. The process of claim 1, wherein the endothelial cells are viable and derived from primary cultures derived from the individual receiving the tissue graft.

36. The process of claim 1, wherein the endothelial cells are viable and derived from cultures derived from an individual not receiving the tissue graft.

37. The process of claim 1, wherein the preconditioning comprises pulsatile flow of nutrient solutions.

38. The process of claim 37, wherein the pulsatile flow mimics pulsatile flow characteristics of the intended site of transplantation.

39. The process of claim 37, wherein the nutrient solutions comprise tissue culture medium.

40. The process of claim 37 wherein the nutrient solutions comprise antioxidants or anti-apoptotic agents.

41. The process of claim 40, wherein the antioxidants are selected from the group consisting of glutathione, glutathione ethylester, cysteine, cystine, ascorbate and butylated hydroxytoluene.

42. The process of claim 40, wherein the anti-apoptotic agents comprise IGF-1, ZVAD1-fink, and thapsigargin.

43. The process of claim 37 wherein the nutrient solutions comprise blood.

44. The process of claim 37 wherein the nutrient solutions comprise additives.

45. The process of claim 44, wherein the additives comprise endothelial growth factor.

46. The process of claim 45, wherein endothelial growth factor is included in the nutrient solutions as a bolus additive remaining in the presence of the tissue graft for periods not to exceed 10 to 60 minutes at a time.

47. The process of claim 44 wherein the additives are selected from the group consisting of essential amino acids, nonessential amino acids, antibiotics, essential vitamins, nonessential vitamins, glycerol, glucose, fructose, lactose, and glutamine.

48. The process of claim 44 wherein the additives comprise growth factors.

49. The process of claim 18 wherein the growth factors are selected from the group consisting of vascular endothelial growth factor, fibroblast growth factor and platelet derived growth factor.

50. The process of claim 1 wherein reendothelializing further comprises the use of a viscous carrier.

51. The process of claim 50, wherein the viscous carrier comprises collagen.

52. The process of claim 51, wherein the collagen is type I, II, III, IV, V, VII, or X.

53. The process of claim 52 wherein the collagen is type I.

54. The process of claim 52 wherein the collagen is type II.

55. The process of claim 52 wherein the collagen is type III.

56. The process of claim 52 wherein the collagen is type IV.

57. The process of claim 52 wherein the collagen is type V.

58. The process of claim 52 wherein the collagen is type VII.

59. The process of claim 52 wherein the collagen is type X.

60. The process of claim 51, wherein the viscous carrier further comprises hyaluronic acid and fibronectin.

61. The process of claim 51, wherein the viscous carrier further comprises endothelial growth factor.

62. The process of claim 51 wherein the viscous carrier further comprises hyaluronin.

63. The process of claim 51 wherein the viscous carrier further comprises laminin and hyaluronin.

64. The process of claim 63 wherein the concentration of collagen, laminim, and hyaluronin is less than 10 weight percent of the viscous carrier.

65. The process of claim 50, wherein the viscous carrier comprises other collagen and laminin.

66. A process for producing a repopulated, reendothelialized, vascular tissue graft, comprising:

obtaining a vascular tissue sample;

eliminating native cellular and extracellular components from said vascular tissue sample, to produce an acellular tissue matrix;

treating said acellular tissue matrix with cell growth factors to produce a treated matrix;

removing basement membrane from a luminal surface of said treated matrix to produce a matrix structure;

repopulating said matrix structure with a fibroblastic cell population to produce a repopulated matrix;

reendothelializing said luminal surface of said repopulated matrix with an endothelial cell population to produce a reendothelialized matrix; and preconditioning said reendothelizlized matrix to promote cell to cell communication and retard apoptotic events, to produce said repopulated, reendothelialized, vascular tissue graft.

67. The process of claim 66 wherein the vascular tissue are derived from human donors.

68. The process of claim 66 wherein the vascular tissue are derived from nonhuman donors.

69. A process for producing a repopulated, reendothelialized, vascular tissue graft, comprising:

obtaining a vascular tissue sample;

eliminating or devitalizing native cellular and extracellullar components from said vascular tissue sample, to produce a tissue matrix;

treating said tissue matrix with cell growth factors to produce a treated matrix;

removing basement membrane from a luminal surface of said treated matrix to produce a matrix structure;

repopulating said matrix structure with a fibroblastic cell population to produce a repopulated matrix;

reendothelializing said luminal surface of said repopulated matrix with an endothelial cell population to produce a reendothelialized matrix; and preconditioning said reendothelizlized matrix to promote cell to cell communication and retard apoptotic events, to produce said repopulated, reendothelialized, vascular tissue graft.

70. The process of any one of claim 66 or 67, wherein said vascular tissue graft is derived from autogenic vascular tissue, allogenic vascular tissue, xenogenic vascular tissue, or tissue engineered vascular tissue.

71. A process for producing a repopulated, reendothelialized, vascular tissue graft, comprising:

obtaining a vascular tissue sample;

eliminating native cellular and extracellular components from said vascular tissue sample, to produce an acellular tissue matrix;

treating said acellular tissue matrix with cell growth factors to produce a treated matrix;

removing basement membrane from a luminal surface of said treated matrix to produce a matrix structure;

repopulating said matrix structure with a fibroblastic cell population to produce a repopulated matrix;

reendothelializing said luminal surface of said repopulated matrix with an endothelial cell population to produce a reendothelialized matrix;

preconditioning said reendothelizlized matrix to promote cell to cell communication and retard apoptotic events, to produce said vascular tissue graft.

72. A process for generating transplantable recellularized and reendothelialized tissue graft, comprising:

decellularizing or devitalizing a tissue sample to produce a matrix structure;

treating said matrix structure with factors to promote viability and function of cells repopulating said matrix structure to produce a treated matrix;

removing the basement membrane from a luminal surface of said treated matrix;

recellularizing said membrane-free matrix with a fibroblastic cell population to produce a fibroblastic matrix;

reendothelializing said luminal surface of said fibroblastic matrix with an endothelial cell population to produce a repopulated tissue; and preconditioning said repopulated tissue to promote cell to cell communication and retard apoptotic events, to produce said tissue graft.

73. A process for producing a recellularized and reendothelialized vascular tissue graft comprising:

obtaining a vascular tissue sample;

eliminating native cellular components from said vascular tissue sample to produce an acellular tissue matrix;

removing basement membrane from a luminal surface of said acellular tissue matrix;

treating said acellular tissue matrix with cell growth factors to produce a treated matrix;

recellularizing said treated matrix structure with a myofibroblastic cell population to produce a recellularized matrix;

reendothelializing the luminal surface of said recellularized matrix to produce a repopulated matrix;

preconditioning said repopulated matrix to promote cell to cell communication, retard apopotosis, and orienate molecular structure of said repopulated matrix to produce said recellularized and reendothelialized vascular tissue graft.

74. A process for producing a repopulated and reendothelialized vascular tissue graft comprising:

obtaining a vascular tissue sample;

eliminating native cellular components from said vascular tissue sample to produce a tissue matrix;

treating said tissue matrix with cell growth factors to produce a treated matrix;

removing basement membrane from a luminal surface of said treated matrix to produce a tissue matrix;

repopulating said tissue matrix with a fibroblastic cell population to produce a repopulated matrix;

reendothelializing a luminal surface of said repopulated matrix to produce a reendothelialized matrix; and preconditioning said repopulated and reendothelialized matrix to promote cell to cell communication, retard apoptosis, and orient molecular structure to produce said repopulated and reendothelialized vascular tissue graft.

* * * * *